United States Patent [19]
Cohen et al.

[11] Patent Number: 5,994,401
[45] Date of Patent: Nov. 30, 1999

[54] IN VIVO METHODS TO REDUCE HYPERCHOLESTEROLEMIA AND IMPROVE VASCULAR DYSFUNCTION

[75] Inventors: Margo P. Cohen, New York, N.Y.; Rex S. Clements, Pineville, Pa.

[73] Assignee: Exocell, Inc., Philadelphia, Pa.

[21] Appl. No.: 09/088,995

[22] Filed: Jun. 2, 1998

Related U.S. Application Data

[63] Continuation-in-part of application No. 08/650,229, May 20, 1996, which is a continuation-in-part of application No. 08/603,147, Feb. 20, 1996, abandoned.

[51] Int. Cl.$^6$ .................................................. A61K 31/24
[52] U.S. Cl. ............................................................ 514/535
[58] Field of Search .............................................. 514/535

[56] References Cited

U.S. PATENT DOCUMENTS 5,643,943  7/1997  Camache et al. ....................... 514/456

OTHER PUBLICATIONS

Embase Abstract 92126412 (1992). Van Boekel et al.
Japanese Abstract 605105615 (1993).

*Primary Examiner*—Zohreh Fay
*Attorney, Agent, or Firm*—Caesar, Rivise, Bernstein, Cohen & Pokotilow, Ltd.

[57] ABSTRACT

The present invention is directed to the prevention in vivo of post-secretory Amadori modifications in the Apo B molecule, as well as methods of using compounds that protect against these modifications in vivo to treat hypercholesterolemia and vascular dysfunction.

7 Claims, No Drawings

IN VIVO METHODS TO REDUCE HYPERCHOLESTEROLEMIA AND IMPROVE VASCULAR DYSFUNCTION

RELATED APPLICATIONS

This application is a continuation-in-part application of pending application Ser. No. 08/650,229, filed on May 20, 1996, entitled "Inhibition of Low Density Lipoprotein Glycation and Treatment of Atherosclerosis", which is incorporated by reference herein, which was a continuation-in-part of ASN 08/603,147, entitled "Prevention of Albumin Glycation and Complications of Diabetes with Albumin-Binding Compounds", now abandoned, also incorporated by reference herein.

TECHNICAL FIELD OF THE INVENTION

This invention is related to the discovery that certain compounds with lipoprotein-binding properties can inhibit the nonenzymatic glycation of apolipoprotein B in vivo. The invention further relates to the ability of such compounds to reduce elevated serum cholesterol concentrations and to prevent the increased urine protein excretion that reflects vascular dysfunction.

BACKGROUND OF THE INVENTION

Apolipoprotein B (apo B) is the principal protein of the cholesterol-carrying low density lipoproteins (LDL) and is the determinant for cellular recognition and uptake of LDL by the high affinity LDL receptor. Binding of apo B to LDL receptors results in internalization and degradation of LDL, promoting the clearance of LDL from plasma and regulating intracellular cholesterol handling and biosynthesis. Post-secretory modification of LDL by oxidation, glycation or glycoxidation diminishes this high affinity LDL-receptor-mediated uptake and degradation (Klein et al, *Diabetes* 44:1093, 1995; Gugliucci et al, *Scand J Lab Clin Invest* 53:125, 1993). On the other hand, such modifications of apo B promote internalization by alternative receptors of monocyte-marcrophages that give rise to cholesterol-laden foam cells (Klein et al, *Metabolism* 38:1108, 1989; Klein et al, *Diabetes* 44:1093, 1995; Brown & Goldstein, *Nature* 343:508, 1990). Additionally, glycation alters the rate of clearance of LDL in vivo and interferes with intracellular handling of cholesterol and regulation of its synthesis, promoting increased serum cholesterol concentrations (Lopez-Virella et al, *Diabetes* 37:550, 1988; Steinbrecher & Witztum, *Diabetes* 33:130, 1984, Lyons et al, *Diabetologia* 30: 916, 1987; Klein et al, *Diabetologia* 33:299, 1990).

Glycated apo B is formed from the condensation reaction between glucose and reactive epsilon amino groups in the apolipoprotein, yielding an amino-deoxyfructose derivative in stable ketoamine linkage known as an Amadori product. It has been proposed that the Amadori product can give rise to a heterogeneous group of poorly defined advanced glycation end products (AGE) resulting from various rearrangement, dehydration and polymerization reactions. Prior art has suggested a pathophysiologic role of AGE-modified LDL in the pathogenesis of elevated LDL-cholesterol and vascular disease, and that inhibition of AGE-crosslink formation might be a beneficial treatment (Brownlee et al, *Science* 232:1629, 1986; *New Engl J Med* 318:1315, 1988; Vlassara, *J Lab Clin Med* 124:19, 1994; Bucala et al, *Proc Natl Acad Sci* 90:6434, 1993; *Proc Natl Acad Sci* 91:9441, 1994). However, recent experimental work as cited above indicates that apo B modified by Amadori products contributes to hypercholesterolemia and vascular dysfunction. Further, glycated LDL principally exists in vivo as the Amadori product and its concentration is elevated in people with increased risk for vascular disease (Cohen et al, *Eur J Clin Chem Clin Biochem* 31:707, 1993; Tames et al, *Atherosclerosis* 93:237, 1992).

The deleterious effects of Amadori-modified apo B make it desirable to have the means to prevent the attachment of glucose to apo B lysine-amino groups in vivo and thereby lower circulating concentrations of modified LDL. It would also be desirable to reduce plasma LDL-cholesterol levels by lowering concentrations of Amadori-modified LDL, thereby promoting LDL cholesterol clearance. Such means would reduce hypercholesterolemia and beneficially influence vascular dysfunction by mechanisms different from those disclosed in the prior art which relate to agents that lower cholesterol levels by inhibiting gastrointestinal absorption or cholesterol synthesis, or that prevent cross-linked AGE-modified LDL. Such means could be achieved with compounds that bind to apo B in a manner that effectively interferes with the modification of free lysine amino groups and thereby inhibit nonenzymatic glycation.

One manner in which post-secretory modification of apo B might be achieved is with compounds that prevent condensation of glucose with lysine amino groups. Acetylsalicylic acid (aspirin), by virtue of rapid acetylation of epsilon amino groups, can competitively inhibit this reaction (Rao and Cotlier, *Biochem Biophys Res Comm* 151:991, 1977; Rendell et al, *J Lab Clin Med* 107:286,1986). However, the impact of widespread protein acetylation is unknown. Moreover, the glycation-inhibiting activity of aspirin is relatively weak and potential therapeutic benefits that might be ascribed to this activity are limited by the rapid hydrolysis and short half-life of acetylsalicylic acid in the blood and by side effects anticipated at doses required to inhibit glycation in vivo (Costello and Green, *Arth Rheum* 25:550, 1982; Rowland and Riegelman, *J Pharm Sci* 57:1313, 1968). Other compounds which lack acetyl groups but bind to albumin in a manner that effectively interferes with the condensation of glucose with free lysine amino groups would be more desirable.

In an in vitro experiment van Boekel et al (*Biochim Biophys Acta* 1120:201, 1991) reported that 2,[2,6-dichlorophenyl-amino]benzene acetic acid (diclofenac) in concentrations of 1–5 mM could reduce the amount of carbohydrate-modified protein after incubation of commercially purchased powdered albumin with 5 mM glucose-6-phosphate (G-6-P). However, van Boekel et al did not examine whether this compound influences carbohydrate attachment to apo B. It is well know that albumin and apo B are proteins that have completely different primary, secondary and tertiary structures. It is also well known that the interaction with, or binding of small molecules to proteins is idiosyncratic and unpredictable. Thus, there is no expectation from the van Boekel reference that this compound could prevent modification of apo B either in vitro or in vivo simply because of impeded attachment of G-6-P to albumin in vitro.

Van Boekel et al conducted only in vitro experiments, only used G-6-P as the modifying substance, and only when the compound was present at 5 mM or more concentration. This concentration of the compound which was required to inhibit G-6-P attachment in vitro, and the composition and concentration of the substance (G-6-P) used to modify the protein, do not represent in vivo conditions. It is well known that although various reducing sugars such as G-6-P can condense with protein amino groups in vitro, the concentrations required vastly exceed those found of such sugars in vivo and that such reducing substances modify proteins in ways that are not representative in chemistry or nature of those which occur in vivo. It is therefore concluded that the compound would not be effective in inhibiting protein glycation in vivo since the primary sugar present in the circulation is glucose, and since the concentrations of the compound required to inhibit glycation in vitro would be toxic if given to living subjects. Diclofenac is usually administered in daily amounts of 100–200 mg. The peak plasma levels obtainable after such dosages are 1–2 µg/ml, which is equivalent to 3–6 µM. This is 1000-fold less than the concentration found by van Boekel et al to achieve any inhibition of albumin glycation in vitro, leading to the conclusion that dosages of 100–200 mg would have no effect on the glycation of any protein in vivo. Van Boekel et al additionally concluded that, because the compound binds to albumin, its concentration in tissues or for preventing modification of other proteins would be too low to be of import in disease states if administered in vivo. Van Boekel et al did not perform any in vivo experiments, does not afford any evidence that the compound could affect glycation in vivo, and contra-indicates the possibility that in vivo administration of therapeutically acceptable amounts of the compound could lower concentrations of modified apo B in living human subjects or could beneficially influence hypercholesterolemia or vascular dysfunction. Additionally, van Boekel et al emphasize that AGE, not Amadori products, are important in vascular disease, leading one to conclude that reducing glycated apo B per se would be without salutary effect in vivo on hypercholesterolemia or vascular disorders. Gamache et al (U.S. pat. No. 5,643,943) have reported the use of esters and amides of pharmaceutical compositions containing an anti-inflammatory and an anti-oxidant moiety for treating inflammatory vascular disorders. Gamache et al teach that a two-pronged approach is necessary in these formulations; namely, the combination of anti-inflammatory and anti-oxidant activity, and that these moieties be covalently linked by an amide or ester bond. The Gamache reference stipulates that compounds that fulfill these requirements are of the formula A—X—$(CH_2)_n$—Y—$(CH_2)_m$—Z wherein A is a nonsteroidal anti-inflammatory agent (NSAIA); A—X is an ester or amide linkage derived from the carboxylic acid moiety of the NSAIA, wherein X is O or NR; R is H, $C_1$-$C_6$ alkyl or $C_5$-$C_6$ cycloalkyl; Y is O, $NR_1$ $C(R)_2$, CH(OH) or $S(O)_n$; n is 2 to 4 and m is 1–4 when Y is O, NR, or $S(O)_n$; n is 0 to 4 and m is 0 to 4 when Y is $C(R)_2$ or is not present; n is 1 to 4 and m is 0 to 4 when Y is CH(OH); n is 0 to 2; and Z is selected from the group of compounds consisting of the formula a, b, c, d or e taught by Gamache et al. Thus, Gamache et al conclude that diclofenac alone, without any amide or ester linked moiety, is useless in the treatment of hypercholesterolemia or vascular disease, and relates only to the synthesis of compounds combining an anti-inflammatory and an anti-oxidant moiety.

The present invention discloses the novel and unexpected discovery that therapeutically acceptable amounts of diclofenac inhibit the formation of glycated apo B in vivo, reduce hypercholesterolemia, and prevent the development of vascular disease which is manifested by increased urine protein excretion in human subjects.

SUMMARY OF THE INVENTION

The present invention provides a means of preventing the nonenzymatic glycation of apo B in living subjects.

This invention is achieved with compounds capable of binding to apo B in the circulation in such a way as to inhibit the condensation of glucose with lysine amino groups in the protein.

The present invention also provides a novel method for reducing the in vivo formation of Amadori-modified apo B that interacts with scavenger receptors.

The present invention also provides a method for treating hypercholesterolemia.

Another embodiment of the present invention provides a method for treating vascular dysfunction manifested by excess urine protein excretion.

Another embodiment of the present invention provides a method for treatment of hypercholesterolernia comprising the step of administering a therapeutic molecule capable of preventing the formation of Amadori adducts in the apo B molecule that interact with scavenger receptors.

Another embodiment of the present invention provides a method for treating vascular dysfunction comprising the step of administering to a patient therapeutic molecule capable of preventing the post-secretory modification of apo B in vivo.

The present invention thus relates to use of compounds that are reactive in vivo with domain(s) in the human apo B molecule and that, by binding to these sites in the structure of apo B, protect the protein against post-secretory modification in vivo.

DETAILED DESCRIPTION

It is a finding of the present invention that compounds that bind to human apo B protect the protein from post-secretory condensation with glucose. This protective action reduces the amount of apo B containing Amadori adducts that is formed upon exposure of the protein to glucose in the circulation in vivo. Reducing the concentration of modified apo B promotes clearance of cholesterol carried in the low density lipoprotein complex and lowers blood cholesterol concentrations. On the basis of this finding, methods are provided for the prevention and treatment of hypercholesterolemia. Post-secretory modification of apo B pathogenetically contributes to increases in serum cholesterol levels and to vascular disease. One of the manifestations of generalized vascular disease is an increase in urine protein excretion (Yudkin et al, *Laucet*, ii:530, 1988; Willey et al, *Diabetes Care* 18: 1502, 1995).

The present invention lowers the serum concentrations of the modified apo B and of cholesterol. A decrease in the modified apo B concentration results in amelioration of LDL-associated pathologic changes in the vasculature. Improvement in vascular dysfunction is associated with reduction in the amount of urine protein excretion.

Compounds which can be administered to humans for these therapeutic uses include those which are capable of binding to sites in the tertiary structure of apo B, which can involve different parts of the primary structure of the protein and which encompass a lysine residue that is a preferential site of nonenzymatic glycation in vivo. One such compound is 2-[2,6-dichlorophenyl)amino]benzene-acetic acid (diclofenac).

Diclofenac has been used as a nonsteroidal anti-inflammatory agent. The usual recommended dose is about 100–200 mg/day in divided doses. For the purposes of the present invention, other doses below and above this range may be employed. It is a weak acid (pKa=4) that is virtually completely absorbed from the gastrointestinal tract with peak levels of approximately 2 µg/ml achieved 2–3 hours after dosing. After absorption, more than 99% of absorbed compound is bound to circulating albumin (Chan et al, *J Pharm Sci* 76:105, 1987).

For treatment and preventative purposes, therapeutic molecules, as described above, can be administered to block sites in apo B that are subject to modification in vivo. By binding to such sites, the therapeutic molecules can prevent the formation of Amadori adducts in apo B, protect against tissue damage which is caused by excess circulating modified apo B, and promote the clearance of LDL cholesterol from the circulation.

Administration according to the methods of the present invention is any method which achieves a sufficient concentration of therapeutic molecule in the circulation or targeted region of the body to be therapeutically useful. Typically such administration will be oral, although parental injection may also be used. Typical doses of therapeutic molecules will achieve effective concentrations of apolipoprotein-binding power. Administration according to the methods of the present invention encompasses doses of 100–300 mg/day and may comprise the therapeutic molecule in a composition with a therapeutically acceptable carrier such as saline solution or in tablet formation, including excipients such as calcium phosphate, starch, sucrose, polyethylene glycol, talc and others.

The above disclosure generally describes the present invention. A more complete understanding can be obtained by reference to the following specific examples which are provided herein for purposes of illustration only, and are not intended to limit the scope of the invention.

EXAMPLE 1
In vivo Protection of Apo B Modification

Plasma samples were obtained from six human subjects at the initiation and termination of 28 days of treatment with diclofenac, 180 mg/day orally in divided doses. The concentration of modified apo B in these samples was determined by analysis in an enzyme linked immunoassay (ELISA) which uses monoclonal antibodies known to specifically react with epitopes containing Amadori adducts that are found on native modified apo B but that are not found on unmodified apo B. The antibodies bind fructosyllysine residues in apo B within the LDL complex. As shown in Table 1, administration of diclofenac produced a 30% reduction in the amount of modified apo B in the circulation.

TABLE I

| Sample | µg/ml Amadori-modified Apo B |
|---|---|
| Baseline | 23.3 |
| Post-treatment | 16.4 |
| Change | (−30%) |

EXAMPLE 2
In vivo Reduction of Serum Cholesterol

Serum samples were obtained from six human subjects at the initiation and termination of 28 days of treatment with diclofenac, 180 mg/day orally in divided doses. Cholesterol concentrations were measured by the cholesterol esterase/cholesterol oxidase method (Sigma Chem Co., St. Louis, Mo.). As shown in Table 2, administration of diclofenac produced a 17% reduction in the serum cholesterol concentration.

TABLE 2

| | Cholesterol (mg/dL) |
|---|---|
| Pretreatment | 242 |
| Post-treatment | 199 |
| Change | (−17%) |

EXAMPLE 3
Lowering Circulating Modified Apo B Improves Vascular Dysfunction

Urine samples were obtained from six human subjects at the initiation and termination of 28 days of treatment with diclofenac, 180 mg/day orally in divided doses. Urine protein excretion was measured by an ELISA immunospecific for albumin and normalized to urine creatinine concentration. Increased urine albumin is associated with vascular disease. As shown in Table 3, administration of diclofenac produced a 52% reduction in albumin excretion.

TABLE 3

| Sample | Urine Albumin µg/mg creatinine |
|---|---|
| Baseline | 60.6 |
| Post-treatment | 26.6 |
| Change | (−52%) |

We claim:

1. A method of treating a living being having hypercholesterolemia which is caused by Amadori-modified Apo B in serum of the living being comprising the steps of: administering in a therapeutically acceptable carrier to the living being a therapeutically effective amount of diclofenac which protects against post-secretory modification of Apo B and lowers the living being's serum concentration of Amadori-modified Apo B.

2. The method of claim 1 wherein diclofenac inhibits the formation of Amadori adducts in the Apo B molecule.

3. The method of claim 2 wherein fructosyllysine modification of Apo B occurs at one or more lysine residues that are preferentially subject to such modification it vivo.

4. The method of claim 1 wherein diclofenac inhibits the formation of modified Apo B epitopes that are recognized by cell-associated scavenger receptors.

5. The method of claim 1 wherein the living being has vascular dysfunction.

6. A method of lowering serum concentrations of Amadori-modified Apo B in a living being comprising the step of administering to the living being a therapeutically effective amount of diclofenac.

7. A method of treating a living being having vascular dysfunction which is reflected by increased protein in the urine of the living being comprising the steps of: administering a therapeutically effective amount of diclofenac of about 100–300 mg/day to the living being which protects against post-secretory modification of Apo B in vivo, lowers the living being's serum concentration of Amadori-modified Apo B, and reduces urine protein excretion.

* * * * *